(12) United States Patent
Lord

(10) Patent No.: US 10,874,149 B2
(45) Date of Patent: *Dec. 29, 2020

(54) ELECTRONIC INHALATION DEVICE

(71) Applicant: Nicoventures Holdings Limited, London (GB)

(72) Inventor: Christopher Lord, London (GB)

(73) Assignee: NICOVENTURES HOLDINGS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/454,127

(22) Filed: Jun. 27, 2019

(65) Prior Publication Data

US 2019/0313700 A1 Oct. 17, 2019

Related U.S. Application Data

(63) Continuation of application No. 14/432,750, filed as application No. PCT/EP2013/071072 on Oct. 9, 2013, now Pat. No. 10,375,990.

(30) Foreign Application Priority Data

Oct. 19, 2012 (GB) .................................. 1218820.7

(51) Int. Cl.
*A61M 15/06* (2006.01)
*A24F 47/00* (2020.01)
(Continued)

(52) U.S. Cl.
CPC ............ *A24F 47/008* (2013.01); *A61M 15/06* (2013.01); *F22B 1/284* (2013.01); *H04W 8/24* (2013.01);
(Continued)

(58) Field of Classification Search
CPC ... A24F 47/008; A61M 15/06; A61M 11/042; A61M 2016/0027; A61M 2205/3375;
(Continued)

(56) References Cited

U.S. PATENT DOCUMENTS 3,200,819 A * 8/1965 Gilbert .................. A61M 15/06
128/202.21
4,947,875 A * 8/1990 Brooks ................. A24F 47/006
128/202.21

(Continued)

FOREIGN PATENT DOCUMENTS

CN 1635920 A 7/2005
CN 102218180 A 11/2013
(Continued)

OTHER PUBLICATIONS

Korean Office Action, Application No. 10-2017-7018345, dated Apr. 25, 2019, 14 pages (27 pages with translation).
(Continued)

*Primary Examiner* — Abdullah A Riyami
*Assistant Examiner* — Vladimir Imas
(74) *Attorney, Agent, or Firm* — Patterson Thuente Pedersen, P.A.

(57) ABSTRACT

An electronic inhalation device comprising a mouthpiece and a control unit, the control unit comprising a power cell and a computer, where the computer comprises a computer processor, a memory and an input-output means; wherein the device further comprises a transmitter connected to the computer and the computer is configured in use to collect and store use data relating to a user's use of the device in the computer memory and transmit the use data.

29 Claims, 5 Drawing Sheets

(51) Int. Cl.
*F22B 1/28* (2006.01)
*H04W 8/24* (2009.01)
*A61M 16/00* (2006.01)
*A61M 11/04* (2006.01)

(52) U.S. Cl.
CPC ... *A61M 11/042* (2014.02); *A61M 2016/0027* (2013.01); *A61M 2205/3375* (2013.01); *A61M 2205/3569* (2013.01); *A61M 2205/3592* (2013.01); *A61M 2205/52* (2013.01); *A61M 2205/8206* (2013.01)

(58) Field of Classification Search
CPC .. A61M 2205/3569; A61M 2205/3592; A61M 2205/52; A61M 2205/8206; H04W 8/24; F22B 1/284
USPC .................................. 439/328, 273; 131/273
See application file for complete search history.

(56) References Cited

U.S. PATENT DOCUMENTS

| | | | | |
|---|---|---|---|---|
| 4,986,269 A * | 1/1991 | Hakkinen | ............ | A61M 16/024 128/200.21 |
| 5,027,837 A | 7/1991 | Clearman | | |
| 5,331,953 A * | 7/1994 | Andersson | ............ | A61M 15/00 128/200.14 |
| 5,363,842 A | 11/1994 | Mishelevich | | |
| 5,894,841 A * | 4/1999 | Voges | ................... | A24F 47/008 128/203.12 |
| 6,196,218 B1 * | 3/2001 | Voges | ................... | A24F 47/002 128/200.14 |
| 6,435,175 B1 * | 8/2002 | Stenzler | ............ | A61M 15/0065 128/200.14 |
| 6,540,672 B1 * | 4/2003 | Simonsen | .......... | A61B 5/14532 600/300 |
| 6,615,825 B2 * | 9/2003 | Stenzler | ............ | A61M 15/0065 128/200.14 |
| 6,729,327 B2 * | 5/2004 | McFarland, Jr. | ....... | A61M 11/02 128/203.12 |
| 6,958,691 B1 * | 10/2005 | Anderson | ............ | A61B 5/0002 340/539.12 |
| 7,547,285 B2 * | 6/2009 | Kline | ..................... | A61B 5/097 600/529 |
| 7,849,851 B2 * | 12/2010 | Zierenberg | ........ | A61M 15/0065 128/200.14 |
| 8,357,114 B2 | 1/2013 | Poutiantine | | |
| 8,453,601 B2 | 6/2013 | Zimmerman | | |
| 8,511,304 B2 | 8/2013 | Anderson | | |
| 8,550,068 B2 * | 10/2013 | Terry | ..................... | A24F 47/008 128/200.12 |
| 8,631,791 B2 * | 1/2014 | Bordewick | ....... | A61M 16/0683 128/206.18 |
| 8,746,240 B2 * | 6/2014 | Terry | ..................... | A61M 15/06 128/200.11 |
| 8,757,147 B2 * | 6/2014 | Terry | ..................... | A24F 47/008 128/202.21 |
| 9,352,108 B1 * | 5/2016 | Reed | ................ | A61M 15/0091 |
| 9,439,455 B2 * | 9/2016 | Alarcon | ................ | A24F 47/008 |
| 9,462,832 B2 * | 10/2016 | Lord | ..................... | H05B 1/0244 |
| 9,724,482 B2 * | 8/2017 | Bach | ................. | A61M 15/0073 |
| 9,782,551 B2 | 10/2017 | Morrison | | |
| 10,065,138 B2 | 9/2018 | Blackley | | |
| 10,159,279 B2 | 12/2018 | Lord et al. | | |
| 10,477,893 B2 | 11/2019 | Lord | | |
| 2003/0212549 A1 | 11/2003 | Steentra | | |
| 2005/0268911 A1 * | 12/2005 | Cross | ................ | A61M 15/0045 128/204.17 |
| 2006/0130860 A1 | 6/2006 | Cholet | | |
| 2007/0045288 A1 * | 3/2007 | Nelson | ............. | A61M 15/0083 219/533 |
| 2008/0194268 A1 | 8/2008 | Koch | | |
| 2008/0257367 A1 | 10/2008 | Petemo | | |
| 2009/0095287 A1 | 4/2009 | Emarlou | | |
| 2009/0095311 A1 * | 4/2009 | Han | ...................... | A24F 47/008 131/194 |
| 2010/0250280 A1 | 9/2010 | Campbell | | |
| 2011/0036346 A1 | 2/2011 | Cohen | | |
| 2011/0265806 A1 | 11/2011 | Alarcon | | |
| 2011/0277756 A1 * | 11/2011 | Terry | .................... | A61M 15/06 128/202.21 |
| 2011/0277760 A1 * | 11/2011 | Terry | .................... | A24F 47/008 128/203.12 |
| 2011/0278189 A1 | 11/2011 | Terry | | |
| 2011/0304282 A1 * | 12/2011 | Li | .......................... | A24F 47/008 315/362 |
| 2012/0048266 A1 | 3/2012 | Alelov | | |
| 2012/0227752 A1 | 9/2012 | Alelov | | |
| 2012/0318882 A1 * | 12/2012 | Abehasera | .......... | A61M 11/041 239/1 |
| 2012/0325227 A1 * | 12/2012 | Robinson | ............ | A61M 16/108 131/328 |
| 2013/0091452 A1 | 4/2013 | Sorden | | |
| 2013/0284192 A1 * | 10/2013 | Peleg | .................... | A24F 47/002 131/329 |
| 2013/0319439 A1 | 12/2013 | Gorelick | | |
| 2013/0319989 A1 | 12/2013 | Liu | | |
| 2014/0007892 A1 | 1/2014 | Liu | | |
| 2014/0060552 A1 * | 3/2014 | Cohen | .................. | A24F 47/008 131/273 |
| 2014/0174459 A1 | 6/2014 | Burstyn | | |
| 2014/0321837 A1 * | 10/2014 | Flick | .................... | F24H 1/0018 392/387 |
| 2015/0136153 A1 | 5/2015 | Lord | | |
| 2015/0181945 A1 | 7/2015 | Tremblay | | |
| 2015/0237917 A1 | 8/2015 | Lord | | |
| 2015/0257448 A1 | 9/2015 | Lord | | |
| 2015/0289565 A1 * | 10/2015 | Cadieux | ................ | A24F 47/002 131/328 |
| 2015/0338235 A1 | 11/2015 | Schmidt | | |
| 2016/0242466 A1 | 8/2016 | Lord | | |
| 2016/0295913 A1 * | 10/2016 | Guo | ................... | B05B 17/0615 |
| 2016/0337141 A1 | 11/2016 | Cameron | | |
| 2017/0035114 A1 | 2/2017 | Lord | | |
| 2017/0035144 A1 | 2/2017 | Parker | | |
| 2018/0280640 A1 | 10/2018 | Baker | | |
| 2019/0133192 A1 | 5/2019 | Lord | | |
| 2020/0138109 A1 | 5/2020 | Lord | | |

FOREIGN PATENT DOCUMENTS

| | | |
|---|---|---|
| EP | 2110034 | 10/2009 |
| JP | 2000-330844 | 11/2000 |
| JP | 2007-034596 | 2/2007 |
| JP | 2008064932 | 3/2008 |
| KR | 1020120027029 | 3/2012 |
| RU | 2360583 C1 | 7/2009 |
| SU | 1837815 A3 | 8/1993 |
| UA | 90256 C2 | 4/2010 |
| UA | 67598 U | 2/2012 |
| WO | WO2000050111 | 8/2000 |
| WO | WO 01/57619 | 8/2001 |
| WO | WO 2007103380 | 9/2007 |
| WO | WO2009134164 | 11/2009 |
| WO | WO2010114392 | 10/2010 |
| WO | WO2011033396 | 3/2011 |

OTHER PUBLICATIONS

Korean Office Action, Application No. 10-2017-7018345, dated Oct. 19, 2018, 10 pages (22 pages with translation).
Japanese Office Action, Application No. 2018-515461, dated Jan. 8, 2019, 4 pages.
Observations Under Article 115 EPC Relating to EP Application No. 13777004.6, dated Nov. 20, 2018, 16 pages.
"Explanatory dictionary of the computation systems", Editor V. Illinguort, M, Machine-building , 1990, 4 pages.
Mostitsky I.L, "English-Russian encyclopedic dictionary of the modern electronic technology and programming: computers, inter-

(56) References Cited

OTHER PUBLICATIONS net, telecommunications, audio-, video-, tele-, radio-technology etc .", Moscow Triumph Publishing House , 2004, 4 pages.

Zhang, J., Huang, Z., Liu, X, Acoustic Communication in Wireless Sensor Networks. In: CS651, Wireless Sensor Networks (D6), pp. 1-8 (Dec. 2005).

Chellis J, Ch. Perkins, M. Stribb, "Foundations of the construction of networks. Manual for the professionals MCSE", M: "LORI", 1997 (D7), 8 pages.

Igoe T: Making Things Talk: Practical Methods for Connecting Physical Objects; "O'Reilly Media, Inc.", Sep. 28, 2007, 1 page.

Erman D: Design and Implementation of an Acoustical Transmission Protocol, Master's Thesis, Blekinge Institute of Technology, Feb. 22, 2002.

Russian Nullity, Application No. 2015114091, dated Jun. 20, 2018, 53 pages.

Patent Examination Report, Application No. 2013331850, dated Dec. 4, 2015, 4 pages.

Fan, Shounian, et al. "Development and research of temporary demand pacemaker with electrocardiosignal display." Journal of biomedical engineering 21.4 (2004): 650-653.

New Progress in Modern Technical Theory and Practice of Underground Mining—a Collection of Theses for Celebrating 50th Anniversary of Beijing Institute of Exploitation under Coal Research Headquarter, Beijing Institute of Exploitation under Coal Research Headquarter, May 2007, p. 318.

Chinese Office Action, Application No. 201380054490.7 , dated May 18, 2018, 14 pages.

Chinese Office Action and Search Report, Application No. 201380054490.7, dated Oct. 9, 2017, 9 pages.

Japanese Office Action, Application No. 2015-537197, dated Jul. 18, 2017, 3 pages.

UA Decision, Application No. 2015 03483, dated Feb. 17, 2016, 8 pages.

Russian Search Report, Application No. 2015114091/12, dated Oct. 10, 2016, 2 pages.

Chinese Office Action, Application No. 201380054490.7, dated Mar. 6, 2017, 1 page.

Application and File History for U.S. Appl. No. 15/764,213, filed Mar. 28, 2018, Inventor: Baker.

Application and File History for U.S. Appl. No. 16/272,187, filed Feb. 11, 2019, Inventor: Baker.

Notice to File a Response from the Korean Patent Office for Korean Application No. 10-2015-7010073 dated Oct. 19, 2016.

Russian Search Report for Russian Application No. 2015114091 dated Aug. 5, 2016.

Zheng et al., "Wireless Sensor Network Technology", Machinery Industry Press. p. 93. Jun. 2012.

Notification of Reasons for Refusal from Korean Patent Office for Korean Application No. 10-2015-7010073 dated Feb. 20, 2017.

Notice of Final Rejection from Korean Patent Office for Korean Application No. 10-2015-7010073 dated Jun. 1, 2017.

International Search report dated Mar. 24, 2014, Application No. PCT/EP2013/071072.

International Preliminary Report on Patentability dated Apr. 21, 2015, Application No. PCT/EP2013/071072.

\* cited by examiner

ELECTRONIC INHALATION DEVICE

RELATED APPLICATION

This application is a continuation of application Ser. No. 14/432,750 filed Mar. 31, 2015, which in turn is a National Phase entry of PCT Application No. PCT/EP2013/071072, filed Oct. 9, 2013, which in turn claims priority to and benefit of United Kingdom Patent Application No. GB1218820.7, filed Oct. 19, 2012, each of which is hereby fully incorporated herein by reference.

TECHNICAL FIELD

The present disclosure relates to electronic inhalation devices. More particularly, but not exclusively, the present disclosure concerns electronic cigarettes comprising a computer and a transmitter.

BACKGROUND

Electronic inhalation devices are typically cigarette-sized and function by allowing a user to inhale a nicotine vapor from a liquid store by applying a suction force to a mouthpiece. Some electronic inhalation devices have a pressure sensor that activates when a user applies the suction force and causes a heater coil to heat up and vaporize the liquid. Electronic inhalation devices include electronic cigarettes.

SUMMARY

An electronic inhalation device comprising a mouthpiece and a control unit, the control unit comprising a power cell and a computer, where the computer comprises a computer processor, a memory and an input-output means; wherein the device further comprises a transmitter connected to the computer and the computer is configured in use to collect and store use data relating to a user's use of the device in the computer memory and transmit the use data.

Storing data has the advantage that data relating to a user's intake and usage habits can be monitored. This is important when the device is used as a replacement for cigarettes since it enables the replacement therapy to be monitored and a determination made as to whether it is working. By transmitting the stored use data, the user is able to transmit the data to a receiving device in order to interpret it and monitor their use of the device.

Suitably, the electronic inhalation device is an electronic cigarette.

Suitably, the computer is a microcontroller.

Suitably, the transmitter is configured to transmit the use data by wireless means.

Suitably, the transmitter is an audio signaling means and is configured to transmit the use data by sound.

Providing a wireless transmission means enables the data to be transmitted and shared without the cumbersome use of a cable interface. This eliminates the need for an access port on the device. Transmitting by wireless means requires a transmitting device within the device. When the transmission is made by sound, the transmitter can be a simple component such as a buzzer or speaker. This is a low cost item yet effective component and allows transmission of data through modulated sound. The sounder can also serve other functions.

Suitably, the use data comprises an inhalation count, where the inhalation count is a count of the number of inhalations a user has taken on the device. Suitably, the inhalation count is stored in 1 byte or 2 bytes of data memory.

Suitably, the use data comprises an average inhalation time, where the average inhalation time is the mean average of the inhalations counted in the inhalation count. Suitably, the average inhalation time is stored in 1 byte or 2 bytes of data memory.

Suitably, the use data comprises a session count, where the session count is a count of the number of inhalation sessions. Suitably, the session count is stored in 1 byte or 2 bytes of data memory. Suitably, an inhalation session ends when the device is inactive for a predetermined inactivity time following inhalation on the device.

By storing data relating to number of inhalations, average inhalation time, and number of sessions, the data storage requirements are minimized yet the important information is still stored. The number of inhalations and number of sessions is just a count and this value can be changed and updated in the computer memory so that only a single value is required. Likewise, the average duration can be changed and updated in the memory so that only a single value is required. Thus the memory space requirements are greatly minimized.

Suitably, the use data is stored in 8 bytes or less of data memory.

Suitably, the use data is optimized for transmission by sound.

Minimizing the data has the advantage that the data can be transmitted more quickly and even repeated transmissions can be made in a short duration so that the user is not waiting for transmissions to be made. Having stored data in 8 bytes or less of data memory provides minimal data for transmission thus speeding up the transmission process. Minimal data may be important when the data is being transmitted by modulated sound.

Suitably, the use data further comprises header data at the start of the data to indicate the start of the data.

Suitably, the use data further comprises footer data that the end of the data to indicate the end of the data.

Suitably, the use data further comprises configuration data towards the start of the data to indicate how the data is configured for transmission.

Suitably, the configuration data indicates the frequency range of the data transmission.

Suitably, the configuration data indicates the duration of the data transmission.

Suitably, the configuration data indicates the intensity of the data transmission.

The extra data provided with the core use data serves to provide useful information to the receiving means about the data being transmitted. Having header data that the receiving means is waiting for ensures that the receiving means knows that data will follow this header data. Likewise, having footer data ensures that the receiving means knows that the data transmission is over. The configuration data is important since it enables the receiver to configure itself and prepare for data being sent. When transmission is by sound, data can be modulated in different frequency ranges, over different time period and will different intensities, so it is an advantage to know how the data will be sent.

Suitably, the use data comprises details of individual inhalation events. Suitably, details of individual inhalation events include the date and time of each inhalation. Suitably, details of individual inhalation events include the duration of each inhalation Suitably, the computer is configured to transmit a first transmission version of the use data and a second transmission version of the use data successively.

Suitably, the first transmission version is substantially the same as the second transmission version.

Suitably, the first transmission version and the second transmission version each has a different frequency range.

Suitably, the first transmission version and the second transmission version each has a different duration.

Suitably, the first transmission version and the second transmission version each has different signal intensity.

Suitably, the computer is configured in use to transmit three or more transmission versions of the use data successively.

Suitably, the computer is configured in use to transmit the use data repeatedly.

By transmitting the data more than once, the receiver is more likely to receive a complete message. If there is interference during one transmission, other transmissions may get through without interference. By varying parameters such as frequency ranges, durations and intensities, the data that is affected under one set of conditions may not be affected under another. Thus, there is a higher chance that the receiver will receive the data. Also, by transmitting the data more that once, the receiver is able to verify the data that is sent.

Suitably, the computer is configured in use to transmit the use data at a frequency substantially above the frequency range of typical background noise.

Suitably, the computer is configured in use to transmit the use data at a frequency substantially above the human hearing frequency range.

There are typical background noises in normal living and working environments. By providing a signal substantially outside of these background noises gives a higher chance that the transmitted signal will be received by the receiver. Also, where the data is transmitted by modulated sound, the transmission noise may be undesirable so providing transmission at a frequency about the human hearing frequency range prevents this.

Suitably, the computer is configured to clear the use data from the memory after transmission.

Suitably, the computer is configured to clear the use data from the memory when controlled to do so by the user.

Once the data has been transmitted, clearing the data from the memory allows future data to be stored.

Suitably, the electronic inhalation device further comprises a pressure sensor connected to the computer.

Suitably, the computer is configured in use to transmit the use data when the pressure sensor detects operation of the device outside of normal use.

Suitably, the computer is configured in use to transmit the use data when the pressure sensor detects blowing into the device.

Suitably, the computer is configured in use to transmit the use data when the pressure sensor detects sucking on the device.

Suitably, the computer is configured in use to transmit the use data the pressure sensor detects a short burst of blowing into the device.

Suitably, the computer is configured in use to transmit the use data when the pressure sensor detects a short burst of sucking on the device.

Suitably, the computer is configured in use to transmit the use data when the pressure sensor detects two or more short bursts of blowing into the device.

Suitably, the computer is configured in use to transmit the use data when the pressure sensor detects two or more short bursts of sucking on the device.

Suitably, the computer further comprises a menu mode configured whereby the pressure sensor is used to activate the menu mode and select a menu option that starts transmission of the use data.

Using the pressure sensor to control the transmission of the data is advantageous since the pressure sensor may already be a feature of the product. Thus, additional components to control the transmission will not be needed. The control is also an internal control so there is less change of it being damaged.

Suitably, the computer is configured to clear the use data from the memory when a user selects a clear memory menu option.

Suitably, the computer is configured to clear the use data from the memory when the menu mode is exited.

Suitably, the computer is configured in use to notify the user by sound when the device has entered the menu mode.

Suitably, the computer is configured in use to notify the user by sound prior to transmission of the use data.

Suitably, the computer is configured in use to notify the user by sound when the transmission of the use data is underway.

Suitably, the computer is configured in use to notify the user by sound when the transmission of the use data is complete.

Suitably, the computer is configured in use to notify the user by sound when the transmission of the use data has been successfully received.

Suitably, the computer is configured in use to notify the user by sound when the transmission of the use data has not been successfully received.

Suitably, the computer is configured in use to notify the user by sound when the use data has been cleared from the computer memory.

Using sound to notify the user has the advantage that a number of different sound signals can easily be used that a user is able to distinguish between. Thus a user can easily identify where transmission has started, ended, succeeded or failed and the user can take action accordingly. This is especially an advantage when the device is controlled using a pressure sensor since the device will be in a user's mouth and a user will find it difficult to look at it. However, when the device is in the mouth, it will be near the user's ears so the sound will be easily heard.

Suitably, the device further comprises a microphone connected to the computer.

Suitably, the computer is configured to determine the background noise using the microphone and transmit the use data so as to substantially avoid the background noise.

Suitably, the computer is configured to start transmission when a start signal is received by the microphone.

Suitably, the computer is configured to end transmission when an end signal is received by the microphone.

Suitably, the computer is configured to retransmit the use data when a fail signal is received by the microphone.

Suitably, the computer is configured to clear the use data from the memory when a clear signal is received by the microphone.

Having a microphone is advantageous since it allows feedback to be received from the receiver and allows control of the transmission by the receiver. Also, a reading can be made of the background noise in order to process the transmission method to provide a transmission that is still able to be received.

Suitably, the electronic inhalation device comprises a mouthpiece end and a tip end, and the transmitter is located at the tip end.

Suitably, the transmitter is configured such that in use the use data is transmitted out of the tip end.

Suitably, the device comprises a longitudinal central axis and the transmitter is configured such that in use the use data is transmitted substantially parallel to the longitudinal axis and out from the tip end.

By setting up the transmission in relation to the physical dimensions of the device, the user is able to orientate the device relative to the receiver in order to optimize the transmission.

Suitably, the transmitter is a speaker.

As used herein the term electronic smoking device includes not only an electronic cigarette but also electronic smoking articles other than an electronic cigarette, for example a heat-not-burn (HNB) device or an electrically powered spray device in which a pressurized liquid is stored in a canister and released under the control of an electronic valve in response to a pressure drop produced by the user drawing on the device. These devices are referred to herein collectively as "electronic smoking devices", which term is intended to cover any electronic device which can be used as a substitute for a cigarette or as a cessation device, which does not involve the conventional combustion of tobacco.

BRIEF DESCRIPTION OF THE DRAWINGS

Embodiments will now be described, by way of example only, with reference to the accompanying drawings in which.

DETAILED DESCRIPTION

Figure 1:
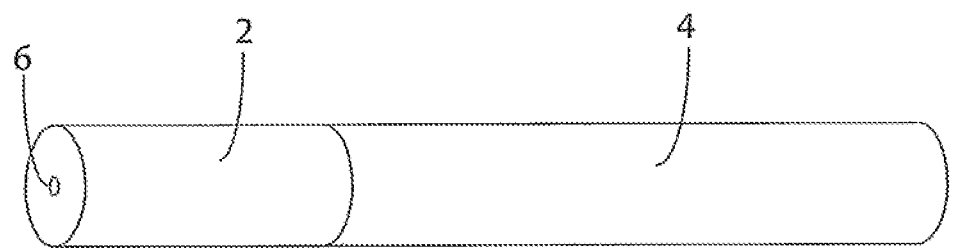
FIG. 1 is a side perspective view of an electronic inhalation device.
Figure 2:
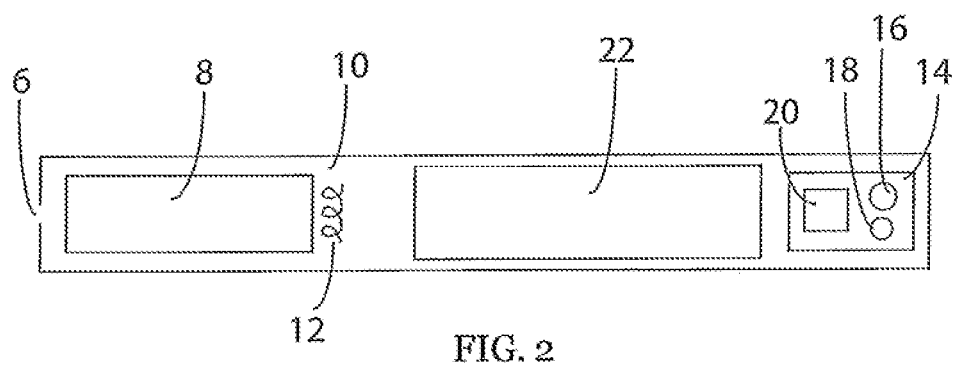
FIG. 2 is a side sectional view through the device of FIG. 1.

Referring to FIG. 1 and FIG. 2 there is shown an electronic inhalation device in the form of a cigarette-shaped electronic cigarette. The electronic cigarette has a mouthpiece 2 and a cigarette body 4. The mouthpiece 2 has an air outlet 6 at a first end and is connected to the cigarette body 4 at a second end.

Inside the electronic cigarette there is a liquid store 8 towards the mouthpiece end and a vaporizer 10 having a heating coil 12. The vaporizer 10 is arranged next to the liquid store 8 to allow liquid to be transferred onto the vaporizer 10 for vaporizing. A circuit board 14 contains a pressure sensor 16, a transmitter 18, and a computer 20. A power cell 22 provides power to the device. The power cell 22 and circuit board 14 with pressure sensor 16, transmitter 18 and computer 20 are contained in a control unit 24.

The general operation of the electronic cigarette is similar to that of known devices. When a user takes a draw on the electronic cigarette, a suction force is applied to the mouthpiece 2 and the air outlet 6. A reduced pressure inside the electronic cigarette causes the power cell 22 to provide power to the vaporizer 10 which in turn vaporizes the nicotine liquid solution. The resultant vapor is then inhaled by the user.

In this example the operation of the electronic cigarette goes beyond that of a general device. In a normal operating mode, when a user applies a suction force to the electronic cigarette, the resultant airflow causes a drop in pressure from ambient pressure to a lower pressure, within the device. The pressure sensor 16 provides a signal to the computer 20. The computer 20 runs software that monitors the pressure signal from the pressure sensor 16 and when it determines that the pressure has been reduced below a threshold pressure, the computer 20 provides an electrical current to the heating coil 12 in order to heat the heating coil 12 and vaporize liquid from the liquid store 8.

The software running on the computer 20 controls the operation of the device. The computer 20 also allows stores data on usage in a memory and allows transmission of this use data.

When a user uses the device in the normal mode of operation to inhale vaporized liquid such as nicotine vapor, the computer 20 monitors this usage. There are three parameters stored by the computer 20. These are the number of inhalations, the average time for an inhalation and the number of sessions.

The number of inhalations is simply a count of the number of times the device is activated to vaporize the liquid solution during normal use. This count starts at zero and is incremented each time the device is activated to deliver vapor during an inhalation. Thus, the count is incremented each time the pressure within the device is reduced below a threshold pressure thereby activating the vaporizer 10. Since this is just a count, the computer 20 stores the number of inhalations value and updates this accordingly. Thus, only a single value is stored in the computer memory.

By definition, 1 byte of data is equal to 8 bits of data. This enables a value between 0 and 255 to be stored in a single byte. In addition, 2 bytes of data enables a value between 0 and 65535 to be stored in two bytes. Thus, the number of inhalations value can easily be stored in 2 bytes of data and possibly 1 byte of data depending on usage.

When a user inhales on the inhalation device and the device activates to heat the heating coil 12 and vaporize the liquid in the liquid store 8, the device is only active while the user is applying a suction force. In fact, the computer 20 determines when the pressure measured by the pressure sensor 16 is reduced below a first threshold pressure value in order to activate the vaporizer 10. When the user ceases inhaling, the pressure within the device increases. The computer 20 determines when the pressure measured by the pressure sensor 16 increases above a second threshold pressure value and deactivates the vaporizer 10, stopping the electrical current flow to the vaporizer 10. The first threshold pressure value and second threshold pressure value are such that the drop in pressure has to be more to activate the device and less to deactivate the device. Thus the first threshold pressure value is a lower absolute pressure than the second threshold pressure value. The pressure change between the first threshold pressure and ambient pressure is greater than the pressure change between the second threshold pressure and ambient pressure. This helps to ensure that the device is not activated accidentally.

The time during which the computer 20 is supplying electrical current to the heating element 12 is an inhalation time. Thus, each inhalation time is dependent on the duration that the user inhales on the device. The computer 20 is able to calculate and store the average inhalation time, being the mean average.

After the first inhalation, the number of inhalations is 1 and the average inhalation time is just the first inhalation time. After the second inhalation, the number of inhalations is 2 and the average inhalation time is the sum of the first and second inhalation times divided by 2. After the nth inhalation, the number of inhalations is n and the average inhalation time is the sum of all inhalations from 1 to n, then divided by n.

The computer 20 is able to update the average inhalation time on each occasion such that it only has to store a single value. In 1 byte of data, the computer 20 can store values between 0 and 25.5 seconds in tenth of a second increments. Since an inhalation typically lasts between 2 and 3 seconds, the average inhalation time can easily be stored in 1 byte of data.

The electronic cigarette replicates the smoking of a real cigarette. A user will typically self-regulate their nicotine intake so whilst the total liquid in the liquid store 8 might provide significantly more nicotine than found in a single cigarette, a user will not inhale all of this at once. A user may use the device in sessions such that a user inhales a number of times in succession but then leaves a bigger time gap than between inhalations before starting again.

When a user inhales on the device, the computer 20 is able to determine the time that has elapsed since the previous inhalation. The computer then determines whether this time is greater than a threshold time period that defines a new smoking session. So if the wait between an inhalation and a subsequent inhalation is greater than a predetermined new session time, the computer identifies the subsequent inhalation as the start of a new session.

The computer 20 is able to count the number of sessions and then update this number as a single value. In 1 byte of data, the computer 20 can store numbers between 0 and 255. In 2 bytes of data, the computer 20 can store numbers between 0 and 65535. Thus the number of sessions can be stored in 1 byte or 2 bytes of data.

As the computer 20 stores use data values, these are updated so that the values are always current following an inhalation. At some point a user may decide to access this information.

A transmitter 18 is connected to the computer 20 and a user can transmit the use data using the transmitter 18. In order to begin transmission, a user must first activate the transmitter 18. There are a number of possibilities for activating the transmission of the data, an example activation makes use of the pressure sensor 16.

The pressure sensor 16 is used in normal operation to inhale a vaporized liquid. So when a user makes use of the pressure sensor in a way not normally used by the pressure sensor, the device can be used to transmit the use data.

When a user has finished using the device and wishes to transmit the use data they can do this by carrying out an action on the device that is different to how they use it in a normal mode. In a normal mode, a user typically inhales on the device for 2 to 3 seconds, replicating the action of smoking a real cigarette. In this situation the computer 20 receives a signal from the pressure sensor 16 and activates the vaporizer 10, heating up the heating coil 12.

To begin transmitting, a user can blow briefly into the device. The pressure sensor 16 sends a signal to the computer 20, and the computer recognizes that this is not normal operation but a signal to begin transmitting. Alternatively a user can blow briefly into the device, suck suddenly on the device in a quick burst or indeed blow or suck two or more times in rapid succession. In each of these circumstances, the pressure sensor 16 will send a signal to the computer 20 and the computer 20 will determine that this is not normal operation but a signal for the device to begin transmitting. When the device leaves normal mode and enters into transmission state, the vaporizer 10 is prevented from activating so that the user can further control the device using the pressure sensor 16 without activating the heating element 12.

The transmitter 18 may be a wireless transmitter therefore transmitting the use data by wireless means to a corresponding receiver. In this example, the transmitter 18 is a sounder such as a buzzer or speaker and transmits the data using sound. The computer 20 interprets the data and causes the transmission of the use data by sound.

Since transmission is generally directional, the transmitter 18 can be oriented and fixed in place relative to the outer cigarette body 4 such that a user is able to determine the transmission direction by looking at the device. In this example, the direction of transmission is out from the tip of the electronic cigarette in a direction parallel to the electronic cigarette.

Thus a user knows that pointing the electronic cigarette at a receiver will give the maximum transmission.

When the transmission is made by sound, a corresponding receiver uses a microphone. In this example, the receiving device is a smart phone having a built in microphone. The smart phone comprises a computer and a software application can be loaded onto the smart phone in order to configure the smart phone to be a receiver for the electronic cigarette transmission.

In use, the electronic cigarette transmits the use data as a sound signal and this sound signal can be detected and recorded on the smart phone. The computer on the smart phone can then extract the data and present this visually to the user.

Since the use data is being transmitted by sound and relies on sound being recorded by the receiving device, any background noise, as is common in most daytime environments, may interfere with the signal and prevent the receiving device from receiving the signal. In order to combat this, the sound signal is broadcast in a frequency range that is outside of most background noise frequency ranges. In another example, because the modulated sound signal may not be a desirable sound for the user, the sound signal could be transmitted at a frequency outside the frequency of human hearing. Thus a user would not heat the sound signal.

In order for the user to identify when a device is ready to transmit, is transmitting and has finished transmitting data, a sound signal corresponding to each of these events is communicated to the user. For example, a single beep may mean ready, a double beep may mean transmitting, and three beeps may mean finished.

Since the use data is only stored in a few bytes of data, this data can easily and quickly be transmitted by modulated sound. There is also the possibility that the data can be transmitted more than once during a transmission session. For example, when a user initiates transmission of the use data, a first version may be transmitted followed directly by a second version, prior to the transmission ending. Any receiving device would be configured to know the number of times that a signal was being transmitted. Having two versions enables two different sound signals to be used to transmit the same data. For example, the second version sound signal could be transmitted at a different frequency, have a different duration, or have a different intensity. This would provide a way to avoid background noise and ensure that the signal and data is received by the receiving device.

In another example, this idea can be taken further and three of more successive version of the data may be transmitted with different sound signals so as to maximise the probability that the receiver receives the signal. In another example, the use data may be transmitted repeatedly until the user stops the signal. This enables the user to position the receiver and wait until the receiving device has successfully received the data.

When a user has finished with the transmission of the data they will want to clear the data from the computer memory so that new data can be stored in the device memory. A user may do this using the pressure sensor 16. Alternatively the computer 20 may assume that the data has been transmitted and automatically clear the memory. A user is notified by a sound signal when the data has been cleared from the computer memory, such as 4 beeps.

In order to help the receiver identify the start and end of the sound signal transmission, header data representing the start of the signal and footer data representing the end of the signal can be added to the use data. Thus, the receiver is able to identify the start of the signal and end of the signal. This is particularly useful when the use data is transmitted more than once.

Figure 3:
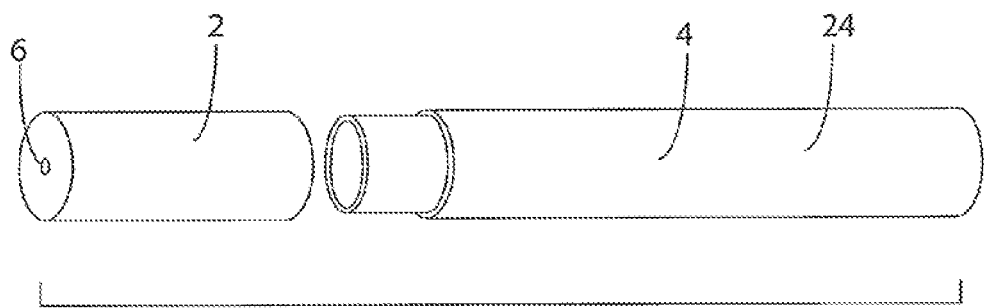
FIG. 3 is an exploded side perspective view of an electronic inhalation device having separated mouthpiece and control unit.
Figure 4:
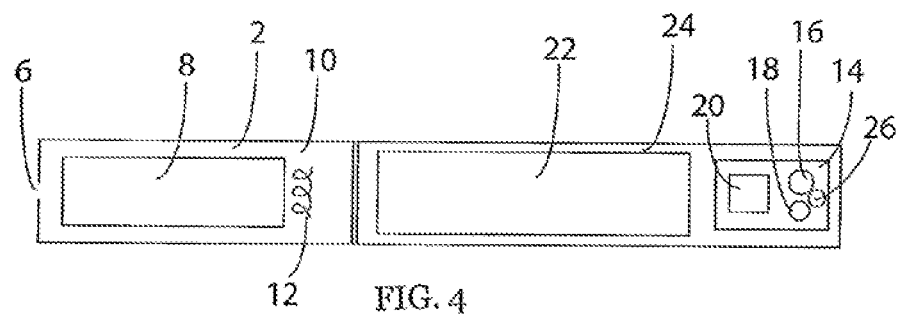
FIG. 4 is a side sectional view through the device of FIG. 3 with connected mouthpiece and control unit.

FIG. 3 and FIG. 4 show a device similar to that shown in relation to FIG. 1 and FIG. 2. The difference is that the mouthpiece 2 is releasably-attachable to the cigarette body 4. The mouthpiece comprises a female screw thread connection means, the cigarette body is a control unit 24 having a male screw thread connection means. The mouthpiece 2 and the control unit 24 can be screwed together or taken apart.

In this example, the mouthpiece 2 comprises the liquid store 8 and the vaporizer 10 with heating coil 12. The control unit 24 comprises the power cell 22 and circuit board 14 with pressure sensor 16, transmitter 18 and computer 20. The screw thread connection provides an electrical connection such that when the mouthpiece 2 and control unit 24 are screwed together, electrical current can be delivered to the heating coil 12 upon activation of the vaporizer 10.

Another difference is that the control unit 24 further comprises a microphone 26. The microphone 26 enables the device to act as both a transmitter and a receiver. In use, the computer 20 is able to measure the background noise using the microphone 26. So rather than providing a use data sound signal that avoids a typical background noise, the computer 20 can configure the sound signal so that it avoids the measured background noise.

The computer 20 is then able to transmit this modified sound signal and there is a higher probability that the receiver will successfully receive the signal. Since the computer 20 is using a measured background noise it may be useful to add configuration data towards the start of the use data sound signal. This configuration data gives information about the signal frequency, duration and intensity to allow the receiver to adjust accordingly in order to receive the transmission.

The microphone 26 also provides a means by which the device can be activated for transmission of the use data. For example, a user could use the receiving device to send out a start sound signal. This would be picked up by the microphone 26 and cause the transmission of the use data to begin. Where the transmission is ongoing, the receiving device could send out a sound signal to end transmission. If the receiving device has not successfully received the use data, it could send out a sound signal to repeat transmission of the use data. If the receiving device has successfully received transmission of the use data is could send out a signal to enable to device to enter normal mode and clear the use data from the memory When the computer 20 identifies that the use data has been transmitted successfully it notifies the user of this by sound. Likewise, when the computer 20 identifies that the use data has not been transmitted successfully it notifies the user of this by sound.

The computer 20 is able to leave the transmitting mode when the vaporizer 10 is unscrewed from the control unit 24.

Figure 5:
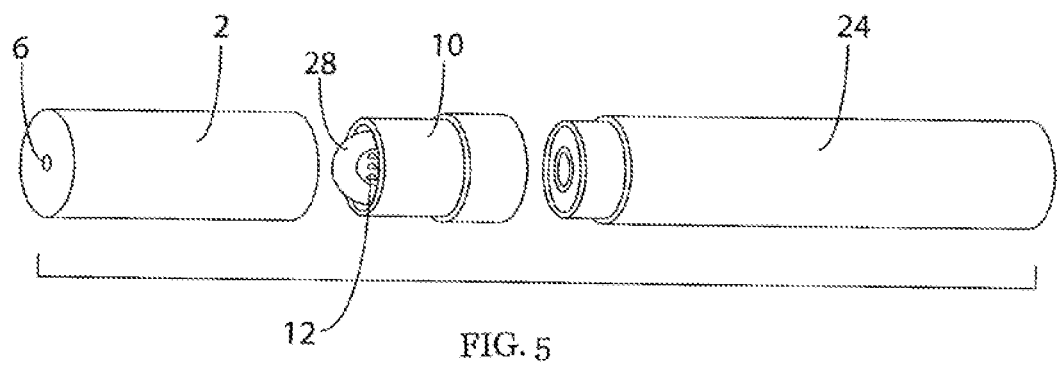
FIG. 5 is an exploded side perspective view of an electronic inhalation device having separated mouthpiece, vaporizer and control unit.
Figure 6:
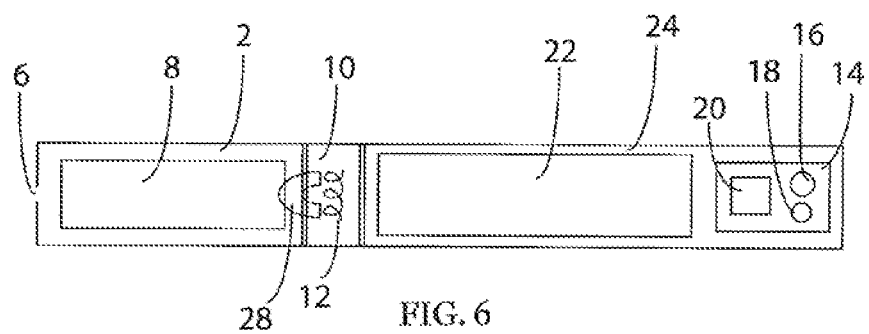
FIG. 6 is a side sectional view through the device of FIG. 5 with connected mouthpiece, vaporizer and control unit.

FIG. 5 and FIG. 6 show a device similar to that shown in relation to FIG. 3 and FIG. 4. However in this example, the vaporizer 10 is removable from the mouthpiece 2. Also, as with the device of FIG. 1 and FIG. 2, there is no microphone on the circuit board 14.

The mouthpiece 2 has a cylindrical opening that forms an interference push-fit with the vaporizer 10. As such the mouthpiece 2 can be separated from the vaporizer 10. The mouthpiece 2 comprises the liquid store 8. The vaporizer 10 comprises the heating coil 12 and a wick 28. The wick 28 protrudes from the end of the vaporizer 10 such that when the mouthpiece 2 and the vaporizer 10 are connected, the wick 28 dips into the liquid store 8.

In use, as a user inhales on the device, liquid is transferred from the liquid store 8 and onto the wick 28 before being transferred onto the heating coil 12 for vaporization.

Figure 7:
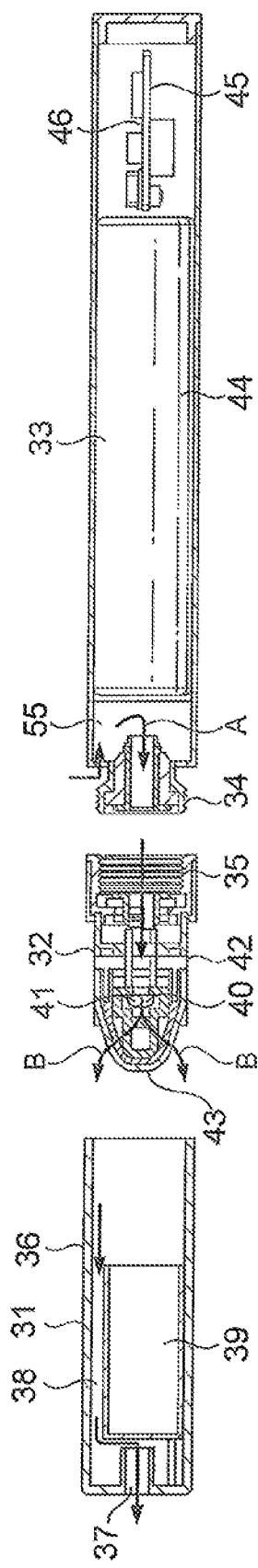
FIG. 7 is an exploded longitudinal sectional view of another embodiment of an electronic inhalation device similar to that of FIGS. 3 and 4, and that of FIGS. 5 and 6, showing the internal components thereof in greater detail.
Figure 8:
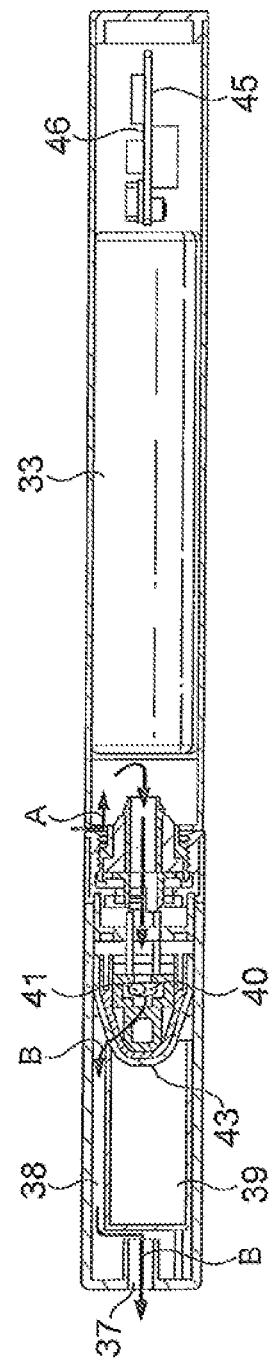
FIG. 8 is a sectional view of the electronic inhalation device of FIG. 7 when assembled.

FIGS. 7 and 8 illustrate another embodiment of an electronic inhalation device in the form of an electronic cigarette. The device is similar to the embodiment shown in FIGS. 3 and 4, and the embodiment shown in FIGS. 5 and 6, although the embodiment in FIGS. 7 and 8 shows the internal components thereof in greater detail. The device comprises a mouthpiece 31, vaporizer device 32 and control unit 33 which can be assembled as shown in FIG. 8 to provide a generally cylindrical device that can be used as a substitute for a conventional tobacco burning cigarette. The control unit 33 is provided with a threaded extension 34 that is received in an interior thread 35 in the vapor device 32. The mouthpiece 31 comprises a generally cylindrical plastics casing 36 that can be push-fitted on to the vapor device 32.

The mouthpiece 31 has an outlet 37 to supply vapor to the mouth of the user and an outlet passageway 38 for the vapor which, in use is produced by the vapor device 32. The mouthpiece 31 also includes a liquid reservoir comprising a porous storage matrix 39 such as plastics open foam material impregnated with a vaporizable liquid, such as a nicotine containing liquid that in use is vaporized by the vapor device 32. The matrix 39 acts as a reservoir for the liquid and since the mouthpiece 31 is readily removable and replaceable, it can be used as a refill capsule when the liquid in the porous matrix 39 becomes depleted and needs to be replenished.

The vapor device 32 includes an electronic heating coil 40 that is wound around a ceramic core 41, supported on a ceramic base 42. A generally U-shaped wicking member 43 is configured to wick liquid from the reservoir 39 towards the heating element 40 by capillary action. The wicking member 43 may for example by made of a metallic foam such as nickel foam.

The heater coil 40 is powered by a rechargeable battery 44 located in the control unit 33 through electrical contacts 48, 49 (not shown in FIGS. 7 and 8, see FIG. 9) which electrically couple the heater coil to the battery 44 when the control unit 33 is fitted to the vapor device 32 by the engagement of threads 34, 35. The electrical power of the battery 44 is supplied to the heater coil 40 under the control of a control circuit 45 mounted on circuit board 46 within the control unit 33.

Figure 9:
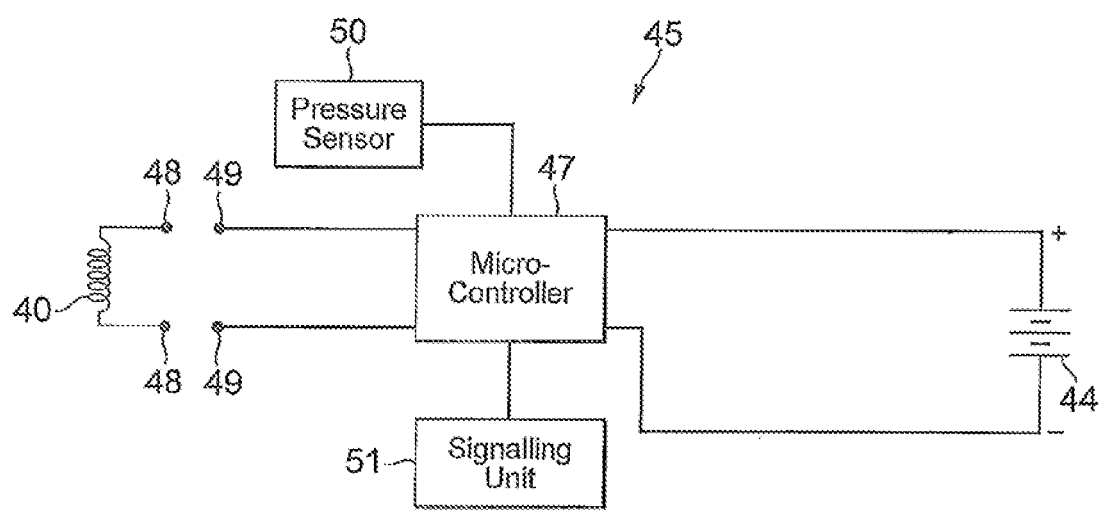
FIG. 9 is a schematic circuit diagram of the electronic inhalation device of FIGS. 7 and 8.

As shown in FIG. 9, the control circuit 45 includes a microcontroller 47 powered by battery 44 to supply an electric heating current to the coil 40 through the contacts 48, 49 that are brought into electrical connection when the control unit 33 is threadedly engaged with the vapor device 32 by means of threads 34, 35 shown in FIG. 7.

A pressure sensor 50 detects when a user draws on the mouthpiece 38, as described in more detail hereinafter.

Also, a signaling unit 51 is provided to provide audio or visual outputs to the user indicative of operational conditions of the device. For example, the signaling device may include a light emitting diode that glows red when the user draws on the device. The signaling device may provide predetermined audio or visual signals to indicate for example that the battery 44 needs to be recharged.

The supply of current from the battery 44 to the mouth controller is controlled by switching transistor 52.

When the user draws on the mouthpiece 1 so as to draw vapor through the outlet 37, the pressure sensor 50 detects the drop in pressure which is communicated from within the vapor device 32 through the interior of the control unit 33 to the circuit board 45. Microcontroller 47 responds to the pressure drop detected by the sensor 50 to supply electrical current to the heater coil 4o, which vaporizes liquid supplied by capillary action through the U-shaped wicking member 43. An air inlet passageway 55 is provided in the joint between the vapor unit 32 and control unit 33 so that air can be drawn through the threaded extension 34 of the control unit 33 into the vapor device 32 in the direction of arrows A, so that the resulting vapor is drawn in the direction of arrows B through passageway 38 to the outlet 37.

The operation of the device of FIGS. 7 and 8 may be the same as that of any of the devices of FIGS. 1 to 6 described previously and so a detailed description of such operation will not be repeated here. However, it is intended that the control circuit 46 of the embodiment of FIGS. 7 and 8 may be configured as per the circuit board 14 of the embodiments of FIGS. 1 to 6, and vice versa. Specifically, the circuit board 46 may comprise a transmitter 18 configured and operable as described previously with respect to the embodiments shown in FIGS. 1 to 6, and so the device may be capable of transmitting usage data and may be activated and/or operated as described previously. Also, the pressure sensor 50 may be disposed on the circuit board 46 within the control unit 33 and the vapor device 32 may be in fluid communication with the area within the control unit 33, via an open passageway for example (not shown), such that a drop in pressure within the vapor device 32 is detectable by a pressure sensor on the circuit board 46 within control unit 33.

In addition to the above, the microcontroller 47 of the embodiment of FIGS. 7 and 8 may be programmed as per the computer 20 of the embodiments of FIGS. 1 to 6 to monitor the measured pressure from the pressure sensor 16 to control the device accordingly and as described previously, particularly to run software to control the operation of the device, including monitor device usage and monitor and calculate the respective usage parameters, as described previously.

The circuit board 46 may further comprise a microphone 26 as per the embodiment shown in FIGS. 3 and 4 and described above, such that the device may act as both a transmitter and a receiver, and function as described in detail above with respect to that particular embodiment.

Although examples have been shown and described it will be appreciated by those skilled in the art that various changes and modifications might be made without departing from the scope of the disclosure. The computer processor could be a microprocessor or a microcontroller. The device is not restricted to being cigarette shaped. The computer processor, transmitter and pressure sensor are not restricted to being on the same circuit board. The heating coil used for vaporization could be replaced by another type of non-coil heating element. The control for the transmitter could be a button or a switch or some other means, rather than the pressure sensor or microphone. The use data could store more information such as details relating to each inhalation including date, time and duration In order to address various issues and advance the art, the entirety of this disclosure shows by way of illustration various embodiments in which the claimed invention(s) may be practiced and provide for superior electronic inhalation devices. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future. Any feature of any embodiment can be used independently of, or in combination with, any other feature.

The invention claimed is:

1. An electronic inhalation device comprising:
   a mouthpiece;
   a control unit comprising a power cell and a computer, the computer including a computer processor, a memory and an input-output; and
   a transmitter connected to the computer,
   wherein the computer is configured to, in use:
      collect and store use data relating to a use of the device by a user in the computer memory, and
      transmit the use data,
   wherein the use data comprises at least one of:
      an inhalation count, and the inhalation count is a count of a number of inhalations a user has taken on the electronic inhalation device,
      an average inhalation time, and the average inhalation time is a mean average of inhalations counted in the inhalation count, or
      a session count, and the session count is a count of a number of inhalation sessions.

2. The electronic inhalation device of claim 1, wherein the electronic inhalation device is an electronic cigarette.

3. The electronic inhalation device of claim 1, wherein the computer is a microcontroller.

4. The electronic inhalation device of claim 1, wherein the transmitter is configured to transmit the use data wirelessly.

5. The electronic inhalation device of claim 1, wherein the transmitter is an audio transmitter configured to transmit the use data by sound.

6. The electronic inhalation device of claim 1, wherein an inhalation session ends when the electronic inhalation device is inactive for a predetermined inactivity time following inhalation on the electronic inhalation device.

7. The electronic inhalation device of, claim 1, wherein the use data is optimized for transmission by sound.

8. The electronic inhalation device of, claim 1, wherein the use data includes at least one of:
   header data at a start of the data to indicate the start of the data;
   footer data at an end of the data to indicate the end of the data; or
   configuration data towards the start of the data to indicate how the data is configured for transmission.

9. The electronic inhalation device of claim 8, wherein the configuration data indicates at least one of: a data transmission frequency range; a data
   transmission duration; or
   an intensity of the data transmission.

10. The electronic inhalation device of claim 1, wherein the use data comprises details of individual inhalation events.

11. The electronic inhalation device of claim 10, wherein details of individual inhalation events include at least one of:
    a date and time of each inhalation; or
    a duration of each inhalation.

12. The electronic inhalation device of claim 1, wherein the computer is configured to transmit a first transmission version of the use data and a second transmission version of the use data successively.

13. The electronic inhalation device of claim 12, wherein the first transmission version is substantially the same as the second transmission version.

14. The electronic inhalation device of claim 12, wherein the first transmission version and the second transmission version each has at least one of:
    a different frequency range;
    a different duration; or
    a different signal intensity.

15. The electronic inhalation device of claim 1, wherein the computer is configured, in use, to do at least one of:
    transmit three or more transmission versions of the use data successively;
    transmit the use data repeatedly;
    transmit the use data at a frequency substantially above a frequency range of typical background noise; or
    transmit the use data at a frequency substantially above the human hearing frequency range.

16. The electronic inhalation device of claim 1, wherein the computer is configured to clear the use data from the memory after transmission.

17. The electronic inhalation device of claim 1, wherein the computer is configured to clear the use data from the memory when controlled to do so by the user.

18. The electronic inhalation device of claim 1, wherein the electronic inhalation device further comprises a pressure sensor connected to the computer.

19. The electronic inhalation device of claim 18, wherein the computer is configured, in use, to transmit the use data when the pressure sensor detects at least one of:
    operation of the electronic inhalation device outside of normal use;
    blowing into the electronic inhalation device;
    sucking on the electronic inhalation device;
    one or more short bursts of blowing into the electronic inhalation device; or
    one or more short bursts of sucking on the electronic inhalation device.

20. The electronic inhalation device of claim 18, wherein the computer is further configured to operate in a menu mode, and the pressure sensor is configured to activate the menu mode and select a menu option that starts transmission of the use data.

21. The electronic inhalation device of claim 20, wherein the computer is further configured to clear the use data from the memory when at least one of:
    a user selects a clear memory menu option; or
    the menu mode is exited.

22. The electronic inhalation device of claim 20, wherein the computer is configured, in use, to notify the user by sound of at least one of: when the electronic inhalation device has entered the menu mode, prior to transmission of the use data, when the transmission of the use data is underway, when the transmission of the use data is complete, when the transmission of the use data has been successfully received, or when the transmission of the use data has not been successfully received.

23. The electronic inhalation device of claim 1, wherein the computer is further configured, in use, to notify the user by sound when the use data has been cleared from the computer memory.

24. The electronic inhalation device of claim 1, wherein the electronic inhalation device further comprises a microphone connected to the computer.

25. The electronic inhalation device of claim 24, wherein the computer is further configured to at least one of:
    determine a background noise using the microphone and to transmit the use data so as to substantially avoid the background noise;
    start transmission when a start signal is received by the microphone;
    end transmission when an end signal is received by the microphone;
    retransmit the use data when a fail signal is received by the microphone; or
    clear the use data from the memory when a clear signal is received by the microphone.

26. The electronic inhalation device of claim 1, wherein the electronic inhalation device further comprises a mouthpiece end and a tip end, and the transmitter is located at the tip end.

27. The electronic inhalation device of claim 26, wherein the transmitter is configured such that, in use, the use data is transmitted out of the tip end.

28. The electronic inhalation device of claim 26, wherein the electronic inhalation device comprises a longitudinal central axis and the transmitter is configured such that, in use, the use data is transmitted substantially parallel to the longitudinal axis and out from the tip end.

29. The electronic inhalation device of claim 1, wherein the transmitter is a speaker.

* * * * *